US009160054B2

(12) United States Patent
Yu et al.

(10) Patent No.: US 9,160,054 B2
(45) Date of Patent: Oct. 13, 2015

(54) RADIO FREQUENCY IDENTIFICATION TAG AND DIAPER, ABSORBER AND SENSING SYSTEM USING THE SAME

(75) Inventors: Jiun-Jang Yu, Tianjhong Township, Changhua County (TW); Chiung-Hsiung Chen, Jhudong Township, Hsinchu County (TW); Chun-An Lu, New Taipei (TW); Hong-Ching Lin, Kaohsiung (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 478 days.

(21) Appl. No.: 13/524,192

(22) Filed: Jun. 15, 2012

(65) Prior Publication Data

US 2013/0123726 A1 May 16, 2013

(30) Foreign Application Priority Data

Nov. 16, 2011 (TW) ............................ 100141919 A

(51) Int. Cl.
*A61F 13/15* (2006.01)
*A61F 13/20* (2006.01)
(Continued)

(52) U.S. Cl.
CPC ............. *H01Q 1/2225* (2013.01); *H01Q 1/273* (2013.01); *H01Q 9/285* (2013.01)

(58) Field of Classification Search
CPC ..... H01Q 1/2225; H01Q 1/273; H01Q 9/285; A61F 13/42; A61F 2013/424; A61B 5/6808
USPC .......................................... 604/361; 340/604
See application file for complete search history.

(56) References Cited

U.S. PATENT DOCUMENTS 4,746,925 A * 5/1988 Toriyama ...................... 343/713
6,603,403 B2 8/2003 Jeutter et al.

(Continued)

FOREIGN PATENT DOCUMENTS

CN 201117797 9/2008
CN 101281615 A 10/2008

(Continued)

OTHER PUBLICATIONS

Um, Y., et al.; "Design of a Compact CPW-Fed UHF RFID Tag Antenna for Metallic Objects;" Microwave and Optical Technology Letters; vol. 50; No. 5; May 2008; pp. 1439-1443.

(Continued)

*Primary Examiner* — Jason Flick
*Assistant Examiner* — Aundria Hairell
(74) *Attorney, Agent, or Firm* — McClure, Qualey & Rodack, LLP

(57) ABSTRACT

A radio frequency (RF) identification tag including a substrate, a planar antenna, an RF chip, a plurality of signal conductors and a plurality of ground conductors is provided. The RF chip receives an RF signal from the planar antenna to generate an identification code. The signal conductors are coupled to the planar antenna. The ground conductors, interlaced on two opposite sides of the signal conductors, and the signal conductors are adjacent to each other and disposed on the substrate to form a coplanar waveguide structure which includes an impedance match portion and a transmission portion. The impedance match portion has an input end coupled to the signal conductors and a ground plane coupled to the ground conductors. The RF chip is disposed between the input end and the ground plane. The transmission portion is connected between the impedance match portion and the planar antenna.

17 Claims, 8 Drawing Sheets

(51) Int. Cl.

| | |
|---|---|
| ***H01Q 1/22*** | (2006.01) |
| ***H01Q 1/27*** | (2006.01) |
| ***H01Q 9/28*** | (2006.01) |

(56) References Cited

U.S. PATENT DOCUMENTS

| | | | |
|---|---|---|---|
| 6,774,800 | B2 | 8/2004 | Friedman et al. |
| 7,083,985 | B2 | 8/2006 | Hefti et al. |
| 7,098,850 | B2 | 8/2006 | King et al. |
| 7,180,423 | B2 | 2/2007 | Forster et al. |
| 7,193,563 | B2 | 3/2007 | King et al. |
| 7,262,740 | B2 | 8/2007 | Tikhov et al. |
| 7,504,998 | B2 | 3/2009 | Choi et al. |
| 8,196,809 | B2 | 6/2012 | Thorstensson |
| 2005/0046578 | A1 | 3/2005 | Pires |
| 2006/0174693 | A1 | 8/2006 | Chen et al. |
| 2008/0074274 | A1 | 3/2008 | Hu et al. |
| 2008/0246616 | A1 | 10/2008 | Sakama et al. |

FOREIGN PATENT DOCUMENTS

| | | | |
|---|---|---|---|
| CN | 101730856 | A | 6/2010 |
| EP | 0 971 227 | | 1/2000 |
| TW | 200814973 | A | 4/2008 |
| TW | 201040891 | A | 11/2010 |
| WO | WO 2009/079326 | | 6/2009 |
| WO | WO 2010/008874 | | 1/2010 |
| WO | WO 2010/009105 | | 1/2010 |

OTHER PUBLICATIONS

Roshayati, M., et al.; "Design of Single Layered Circular and Rectangular U-Slotted, CPW-Fed Antennas and Arrays for RFID Applications;" Fourth Asia International Conference on Mathematical/Analytical Modelling and Computer Simulation; 2010; pp. 571-574.

Yang, L., et al.; "A Novel Conformal RFID-Enabled Module Utilizing Inkjet-Printed Antennas and Carbon Nanotubes for Gas-Detection Applications;" IEEE Antennas and Wireless Propagation Letters; vol. 8; 2009; pp. 653-656.

Jia, Y., et al.; "A Prototype RFID Humidity Sensor for Built Environment Monitoring;" International Workshop on Education Technology and Training; 2008; pp. 496-499.

Siden, J., et al.; "Microstrip Antennas for Remote Moisture Sensing using Passive RFID;" IEEE; 2009; pp. 2375-2378.

Siden, J., et al.; "Remote Moisture Sensing utilizing Ordinary RFID Tags;" IEEE Sensors; 2007; pp. 308-311.

Arbulante, M.L., et al.; "RFID-Based Humidity Monitoring System for Food Storage Areas;" ECE Student Conference; Mar. 2010; pp. 1-6.

CN Office Action dated Mar. 30, 2015 in corresponding Chinese application (No. 201110430744.3).

TW Notice of Allowance dated Jan. 20, 2015 in corresponding Taiwan application (No. 100141919).

Xingwen, et al.: "Research on Automatic Matching Technology for Antenna Impedance Based on RFID"; Chinese Journal of Electron Devices; vol. 33, No. 2, Apr. 2010; pp. 1-5.

* cited by examiner

RADIO FREQUENCY IDENTIFICATION TAG AND DIAPER, ABSORBER AND SENSING SYSTEM USING THE SAME

This application claims the benefit of Taiwan application Serial No. 100141919, filed Nov. 16, 2011, the disclosure of which is incorporated by reference herein in its entirety.

BACKGROUND

1. Technical Field

The disclosed embodiments relate in general to a diaper, an absorber and a wetness sensing system, and more particularly to a radio frequency (RF) identification tag with coplanar waveguide structure, and a diaper, an absorber and a sensing system using the same.

2. Description of the Related Art

In general, diapers and urine pads, whether being used by infants, the elder with disabilities, or even the invalid, must be replaced frequently, otherwise the users may be susceptible to diaper rash or skin disease, which may even progress into a urinary tract infection. A long-term care institution, overcrowded with those under care and suffering from a shortage of nursing personnel, is incapable of immediately identifying which of those under care needs to change his/her diaper, and the risk of urinary tract infection is thus increased. On the other hand, a center-wide, manual check-up is far inefficient.

When a conventional disposable paper diaper or paper urine pad gets wet, one must typically touch the diaper or pad to determine whether the diaper or the urine pad is too wet and needs to be replaced. Currently, some paper diapers have a color rendering structure which develops a specific color or pattern when the paper diaper gets wet. One can determine whether to change the paper diaper according to the developed color or pattern without having to touch the diaper physically. For all currently available paper diapers, inclusive of the diapers with color rendering structure, one still has to take initiative to check frequently whether urine wetness is indicated, and this is indeed a great burden and pressure to the parents or caregivers. It is desired to provide a diaper or urine pad system that overcomes these or other disadvantages.

SUMMARY

The disclosure is directed to a radio frequency (RF) identification tag and a diaper, an absorber and a sensing system using the same. The antenna portion and the sensor unit (that is, the impedance match portion) of the RF identification tag are separated by a predetermined distance to promote a stable signal reading and meet the requirements of wetness sensing.

According to one embodiment, a radio frequency (RF) identification tag including a substrate, a planar antenna, an RF chip, a plurality of signal conductors and a plurality of ground conductors is provided. The RF chip receives an RF signal from the planar antenna. The signal conductors are coupled to the planar antenna. The ground conductors, interlaced on two opposite sides of the signal conductors, and the signal conductors are adjacent to each other and disposed on the substrate to form a coplanar waveguide structure, which includes an impedance match portion and a transmission portion. The impedance match portion has an input end and a ground plane. The input end is coupled to the signal conductors, and the ground plane is coupled to the ground conductors. The RF chip is disposed between the input end and the ground plane. The transmission portion is connected between the impedance match portion and the planar antenna.

According to another embodiment, a wetness sensing diaper including the said RF identification tag with coplanar waveguide structure is provided.

According to an alternative embodiment, a wetness sensing absorber including the said RF identification tag with coplanar waveguide structure is provided.

According to another alternative embodiment, a wetness sensing system including the said RF identification tag with coplanar waveguide structure is provided.

The above and other aspects of the disclosure will become better understood with regard to the following detailed description of the non-limiting embodiment(s). The following description is made with reference to the accompanying drawings.

Figure 1B:
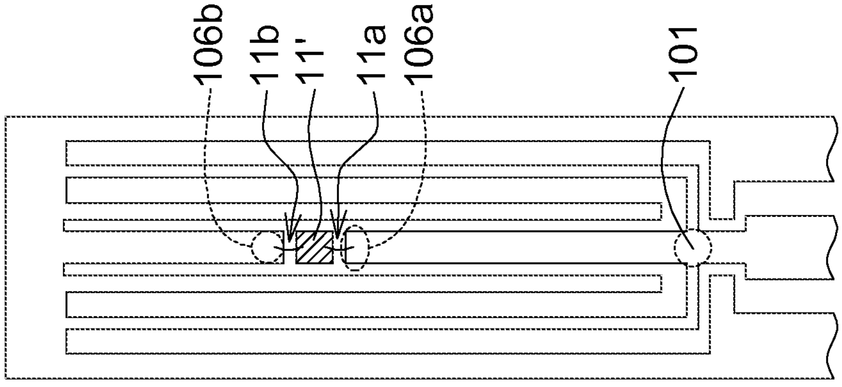
FIGS. 1A and 1B respectively are schematic diagrams of coplanar waveguide structures according to an embodiment of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

According to an embodiment of a radio frequency (RF) identification tag and a diaper, an absorber and a sensing system using the same, an RF signal transmission line and two ground transmission lines of the coplanar waveguide structure are used in the RF identification tag for providing urine wetness sensing function or wetness sensing function. The RF identification tag does not require external power, hence reducing risk of electrical shock. The coplanar waveguide structure includes an impedance match portion and a transmission portion. The RF chip is disposed in the impedance match portion. The transmission portion is connected between the planar antenna and the impedance match portion. The differences between the RF identification tag of the present embodiment and an ordinary RF identification tag are described below.

The sensor unit of the ordinary RF identification tag is the radiator whose resonant frequency is affected by the dielectric constant of the material and the length of the radiator cannot be extended. When the RF identification tag is disposed in the wetness sensing area of a diaper or an absorber, the RF identification signal may easily be shielded by the human body. Therefore, the ordinary RF identification tag cannot achieve stable signal readings and meet the requirements of wetness sensing. The RF identification tag of the present embodiment uses the impedance match portion as a sensor unit, and may be disposed in the wetness sensing area of a diaper or an absorber. The RF identification tag of the present embodiment includes a transmission portion, and the design with the impedance match portion being located in the sensing area (such as the urine wetness sensing area) and the planar antenna being located in the reading area can thus be achieved.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

First Embodiment

Figure 1A:
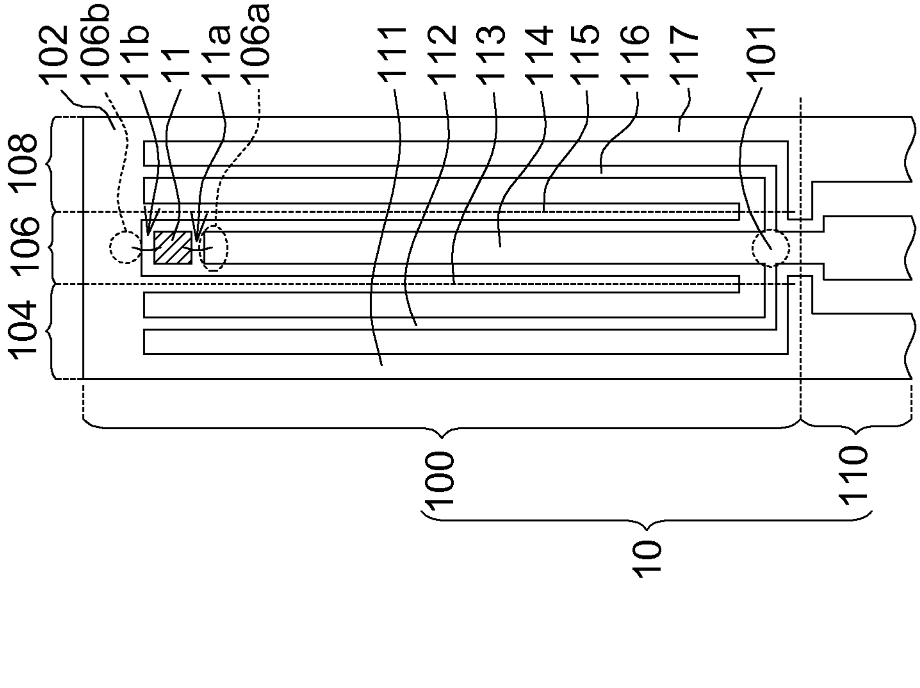

Referring to FIGS. 1A and 1B, schematic diagrams of coplanar waveguide structures according to an embodiment of the disclosure are shown. The coplanar waveguide structure 10 includes an impedance match portion 100 and a transmission portion 110. The impedance match portion 100 has an input end 101 and a ground plane 102. The impedance of the input end 101 matches the input impedance of the transmission portion 110. The interior of the impedance match portion 100 at least includes three neighboring transmission lines, namely, a first shorted transmission line 104, an RF signal transmission line 106 and a second shorted transmission line 108 arranged from left to right in sequence. The three neighboring transmission lines are respectively formed by a plurality of neighboring metal conductors, namely, a first ground conductor 111, a first signal conductor 112, a second ground conductor 113, a second signal conductor 114, a third ground conductor 115, a third signal conductor 116 and a fourth ground conductor 117 arranged from left to right in sequence. The first ground conductor 111, the second ground conductor 113, the third ground conductor 115 and the fourth ground conductor 117 respectively have one end coupled to the ground plane 102 to form a common ground plane.

The first signal conductor 112 is coupled between the input end 101 and the ground plane 102. The first signal conductor 112 and its neighboring ground conductors, that is, the first ground conductor 111 and the second ground conductor 113, together constitute a first shorted transmission line 104. The second signal conductor 114 is coupled between the input end 101 and the ground plane 102. The second signal conductor 114 and its neighboring ground conductors, that is, the second ground conductor 113 and the third ground conductor 115, together constitute an RF signal transmission line 106. The RF signal transmission line 106 has two contacts 106*a* and 106*b* respectively coupled to the first and the second ends 11*a* and 11*b* of the RF chip 11. The third signal conductor 116 is coupled between the input end 101 and the ground plane 102. The third signal conductor 116 and its neighboring ground conductors, that is, the third ground conductor 115 and the fourth ground conductor 117, together constitute a second short-circuiting transmission line 108.

The RF chip 11 is disposed on the RF signal transmission line 106 located between the input end 101 and the ground plane 102. The contacts 106*a* and 106*b* of RF signal transmission line 106 have an input impedance. The input impedance (R+jX) of the RF identification tag and the complex impedance (R−jX) of the RF chip 11 are conjugate and match each other.

Referring to an embodiment illustrated in FIG. 1B. By adjusting the position of the RF chip 11' on the RF signal transmission line 106, the matching bandwidth between the RF chip and the RF identification tag can be adjusted, and the sensing sensitivity of the RF identification tag can be fine-tuned through the adjustment in the matching bandwidth.

Second Embodiment

Figure 2B:
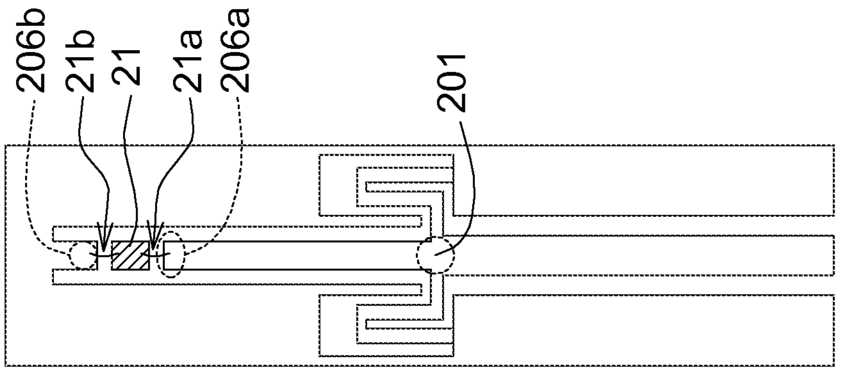
FIGS. 2A and 2B respectively are schematic diagrams of coplanar waveguide structures according to an embodiment of the disclosure.
Figure 2A:
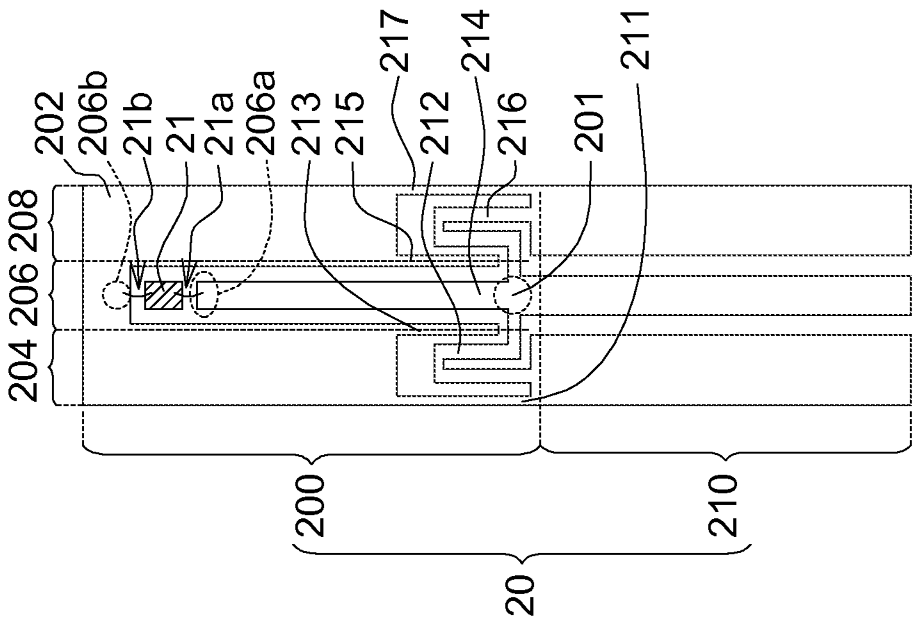

Referring to FIGS. 2A and 2B, schematic diagrams of coplanar waveguide structure 20 according to an embodiment of the disclosure are shown. The coplanar waveguide structure 20 includes an impedance match portion 200 and a transmission portion 210. The differences between the impedance match portion 200 of the present embodiment and the impedance match portion 100 of the first embodiment are as follows. In the present embodiment, the first signal conductor 212 and the third signal conductor 216 are extended in an S shape instead of a long strip. The ground plane 202, extended to two opposite sides of the second signal conductor 214, is coupled to the first ground conductor 211, the second ground conductor 213, the third ground conductor 215, and the fourth ground conductor 217 respectively to from a common ground plane. The first signal conductor 212 is coupled between the input end 201 and the first ground conductor 211. The first signal conductor 212 and its neighboring ground conductors, that is, the first ground conductor 211 and the second ground conductor 213 and the ground plane 202, together constitute a first shorted transmission line 204. The second signal conductor 214 is coupled between the input end 201 and the ground plane 202. The second signal conductor 214 and its neighboring ground conductors, that is, the second ground conductor 213 and the third ground conductor 215 and the ground plane 202, together constitute an RF signal transmission line 206. The third signal conductor 216 is coupled between the input end 201 and the fourth ground conductor 217. The third signal conductor 216 and its neighboring ground conductors, that is, the third ground conductor 215 and the fourth ground conductor 217, and the ground plane 202 together constitute a second shorted transmission line 208.

Since the second ground conductor 213 and the third ground conductor 215 of the present embodiment are shorter than the second ground conductor 113 and the third ground conductor 115 of the first embodiment, the potential in common ground plane is more uniform in the present embodiment than in the first embodiment. When the match portion is enlarged (to increase the sensing area) by serially connecting to other transmission lines, the impedance characteristics of the impedance match portion 200 still can be maintained.

In the present embodiment, the RF chip 21 is disposed on the RF signal transmission line 206. The RF chip 21 has a first end 21*a* and a second end 21*b*, which are respectively coupled to the contacts 206*a* and 206*b* of the RF signal transmission line 206. The contacts 206*a* and 206*b* of the RF signal transmission line 206 have input impedance. The input impedance (R+jX) of the RF identification tag and the complex impedance (R−jX) of the RF chip 21 are conjugate and match each other.

Figure 3A:
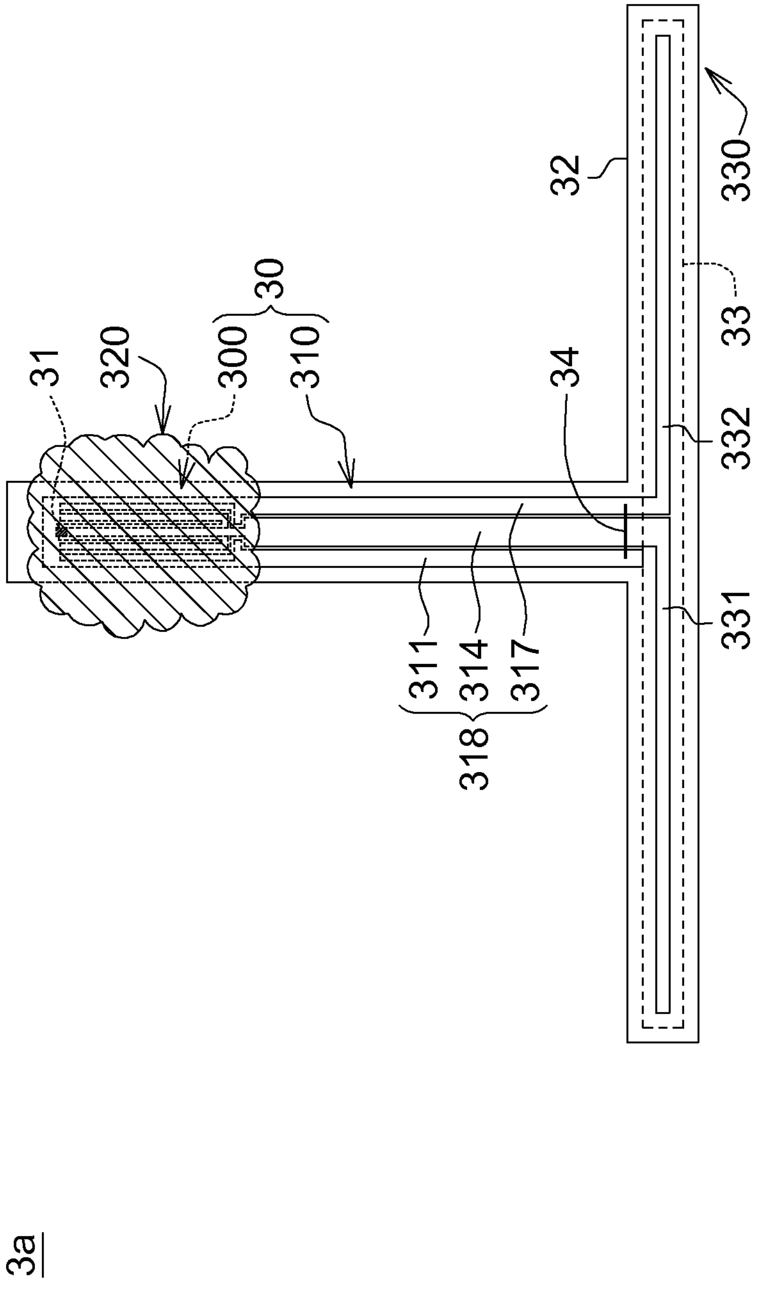
FIGS. 3A-3C respectively are schematic diagrams of RF identification tags according to different embodiments.
Figure 3B:
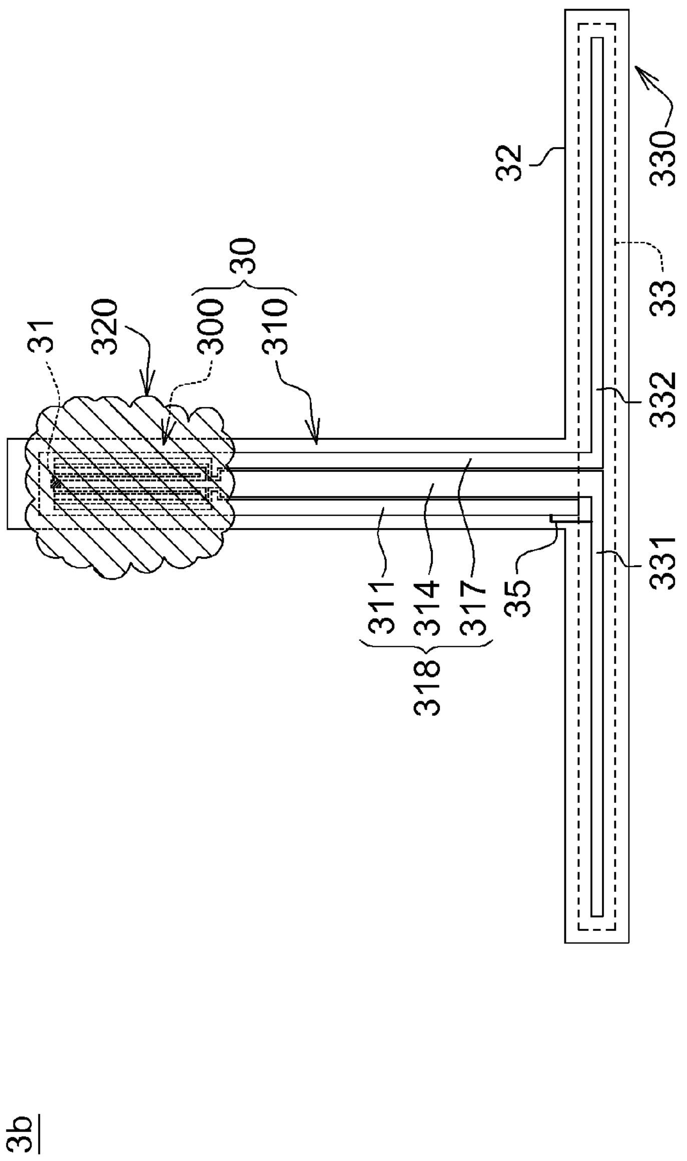
Figure 3C:
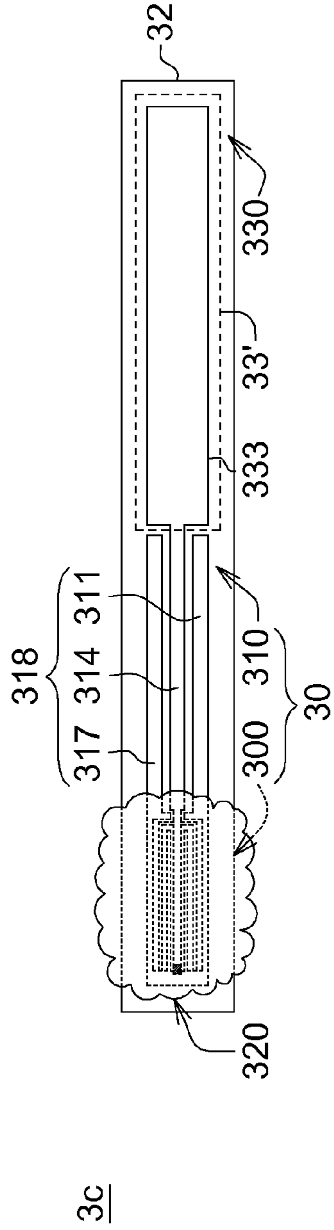

Referring to FIGS. 3A-3C, schematic diagrams of an RF identification tag according to different embodiments are shown. In each embodiment, the coplanar waveguide structure 10 or 20 illustrated in FIGS. 1A and 1B and FIGS. 2A and 2B can be used in the RF identification tag. Therefore, detailed descriptions of the impedance match portion 300 (equivalent to the impedance match portion 100 or 200) are omitted in the following descriptions of different embodiments, and only the disposition relationships among the substrate 32, the planar antenna 33 and the transmission portion 310 of the coplanar waveguide structure 30 are disclosed below.

The planar antenna 33 is disposed on the substrate 32. In the part of the transmission portion 310, the first ground conductor 311 and the fourth ground conductor 317 are respectively disposed on two opposite sides of the second signal conductor 314 to constitute an RF signal transmission line 318. The RF signal transmission line 318 is coupled between the planar antenna 33 and the impedance match portion 300 for transmitting the RF signal. In the present embodiment, the transmission portion 310 of the coplanar waveguide structure 30 is integrally connected between the impedance match portion 300 and the planar antenna 33. The impedance match portion 300 is located in the sensing area 320 (such as the urine wetness sensing area). As the characteristic impedance of impedance match portion 300 varies with the volume of urine, the matching characteristics will drift and the receiving energy of the RF chip 31 will be affected.

When the receiving energy is too small to excite the RF chip 31, the sensing purpose will be achieved. Also, the characteristic impedance of the coplanar waveguide structure 30 is very sensitive with the thickness and permittivity of the dielectric material. Using the impedance match portion 300 as a wet sensor can increase the sensitivity in wetness detection. However, the RF identification tags 3*a*-3*c* of the present embodiment of the disclosure is not limited to sensing urine wetness, and may also be used in sensing relevant humidity.

In addition, the length of the transmission portion 310 is adjustable and ranges between 1-30 cm. Therefore, the impedance match portion 300 being located in the urine wetness sensing area 320 and the planar antenna 33 being located in the reading area 330 is achieved, and the performance of the planar antenna 33 will not be affected by urine, wetness or other environmental factors. Consequently, the RF identification tags 3*a*-3*c* of the present embodiment may both achieve stable signal reading and meet the requirements of wetness sensing.

As shown in FIG. 3A, the planar antenna 33, realized by a dipole antenna, includes a first radiator 331 and a second radiator 332. The first radiator 331 connects with the second signal conductor 314. The second radiator 332 connects with the fourth ground conductor 317. A jumper 34 crosses over the first ground conductor 311 and the fourth ground conductor 317. In addition, as shown in FIG. 3B, a ¼ wavelength ground conductor 35 replaces the jumper 34 and connects the first ground conductor 311 and the second signal conductor 314, not only maintaining uniform distribution of the currents for the first ground conductor 311 and the fourth ground conductor 317 but also reducing the variation in characteristic impedance for the RF signal transmission line 318. As shown in FIG. 3C, the planar antenna 33', realized by a monopole antenna, includes a radiator 333 which connects the second signal conductor 314.

Figure 3D:
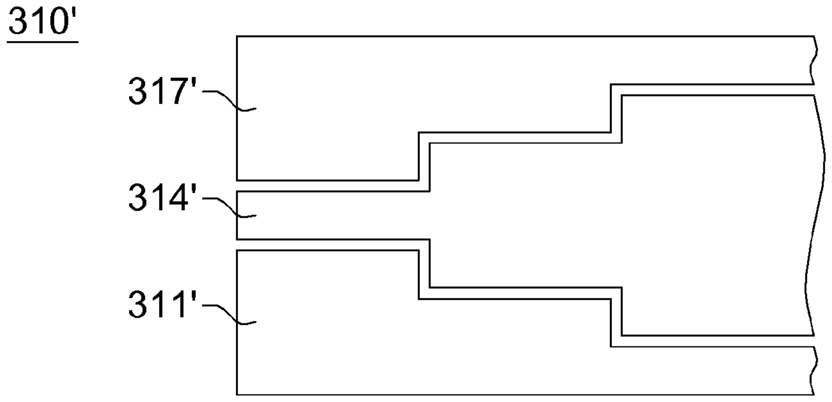
FIG. 3D shows a partial schematic diagram of a transmission line according to an embodiment.

As shown in FIGS. 3A-3C, the second signal conductor 314, the first ground conductor 311 and the fourth ground conductor 317 that are located in the transmission portion 310 may adjust their relative width according to the required impedance. Referring to FIG. 3D, a partial schematic diagram of a transmission line 310' according to an embodiment is shown. The width of the second signal conductor 314' may shrink in the shape of a ladder along the linear direction to obtain ladder type impedance. Similarly, the widths of the first ground conductor 311' and the fourth ground conductor 317' located on two opposite sides of the second signal conductor 314' may also shrink in the shape of a ladder. Therefore, through the adjustment in the widths of the signal conductors of the RF signal transmission line or the intervals between the signal conductors and the ground conductors, the impedance of the input end matches the input impedance of the transmission line 310'.

Application Example

Figure 4A:
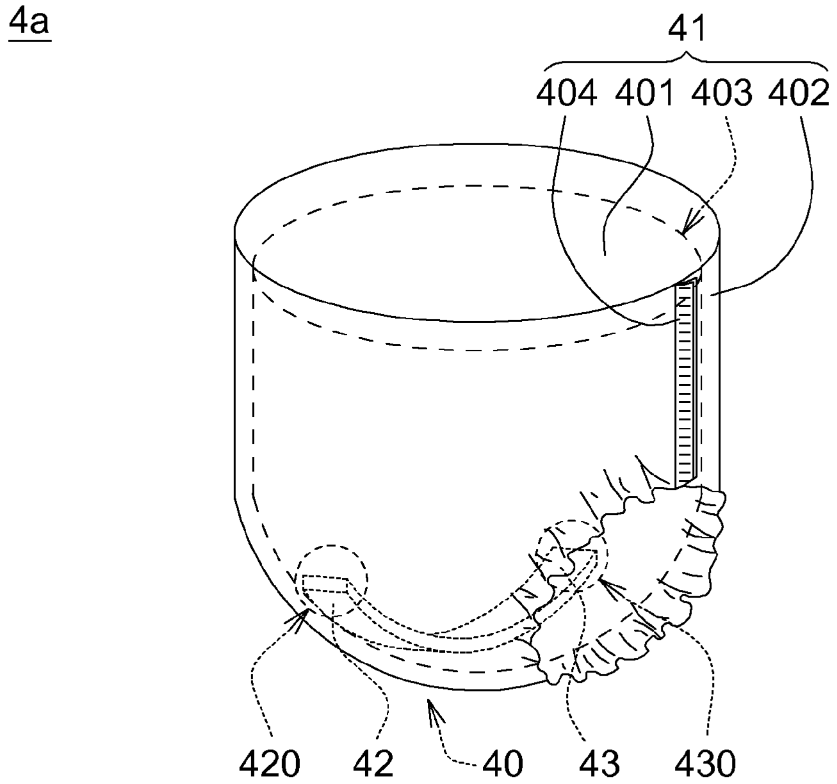
FIGS. 4A-4B respectively are schematic diagrams of wetness sensing diapers according to an application example of the disclosure.
Figure 4B:
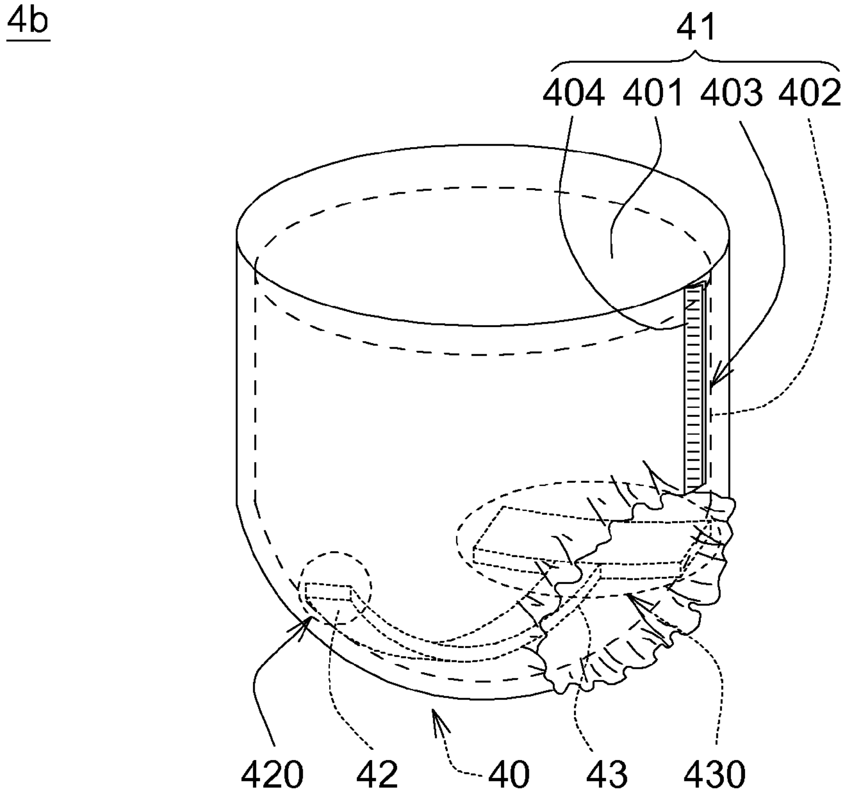
Figure 5A:
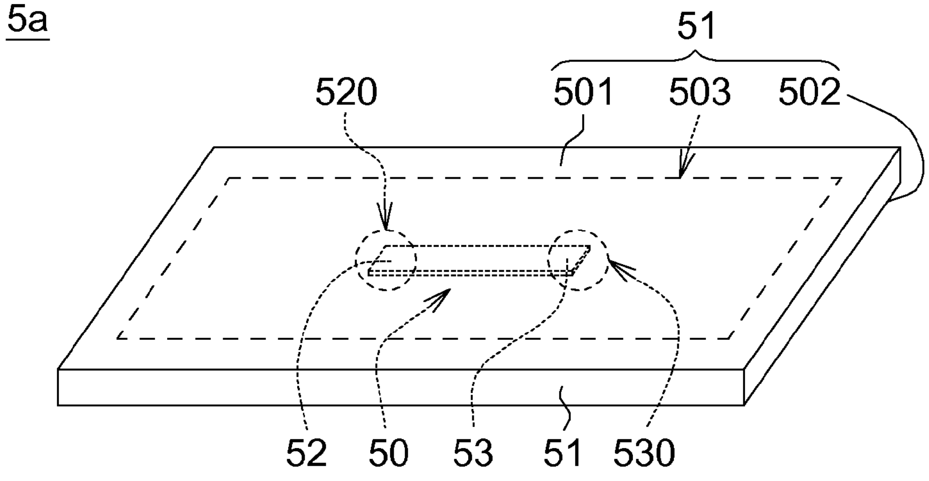
FIGS. 5A-5B respectively are schematic diagrams of wetness sensing absorbers according to another application example of the disclosure.
Figure 5B:
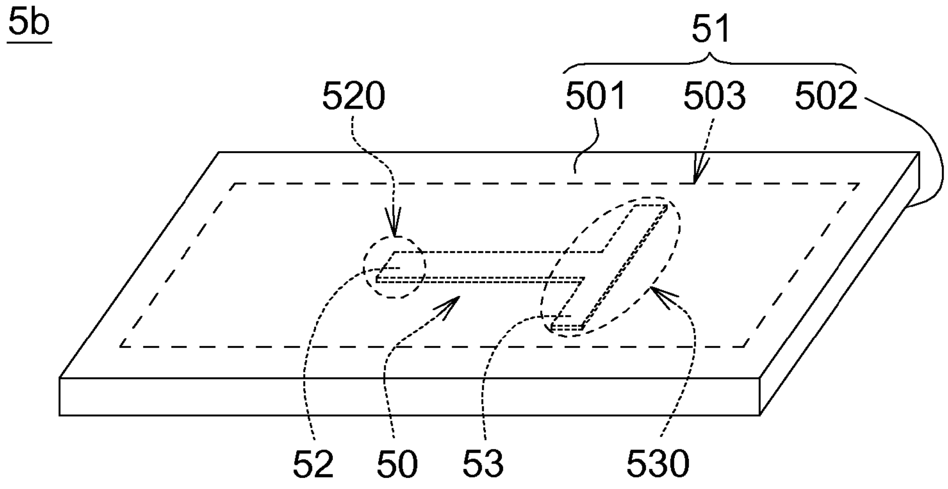

Referring to FIGS. 4A-4B and 5A-5B. FIGS. 4A-4B respectively are schematic diagrams of wetness sensing diapers according to an application example of the disclosure. FIGS. 5A-5B respectively are schematic diagrams of wetness sensing absorbers according to another application example of the disclosure. In each application example, any of the RF identification tags 3*a*-3*c* illustrated in FIGS. 3A-3C may be used in the urine wetness sensing diapers 4*a*-4*b* or the wetness sensing absorbers 5*a*-5*b*. The designations inside and outside a parentheses are used for different application examples. The body 41 of the wetness sensing diapers 4*a*-4*b* and the body 51 of the wetness sensing absorbers 5*a*-5*b* respectively include an inner layer 401 (501), an outer layer 402 (502) and an absorber 403 (503). The inner layer 401 (501) is liquid permeable to keep the surface dry and cozy. The outer layer 402 (502) is liquid impermeable and is formed by such as a waterproof PE film such blocks the leakage of water. The absorber 403 (503) is interposed between the inner layer 401 (501) and the outer layer 402 (502) to absorb urine or water. The wetness sensing diapers 4*a*-4*b* may further include a cingulum 404, which fixes the diaper on the waist so that the user would have more freedom in mobility and would find it easier in changing the diaper.

In the two application examples, the RF identification tag 40 (50) is located in the urine wetness sensing diapers 4*a*-4*b* (or the wetness sensing absorbers 5*a*-5*b*) and is disposed between the inner layer 401 (501) and the outer layer 402 (502). When urine (or water) permeates to the absorber 403 (503) through the inner layer 401 (501), the characteristic impedance of the impedance match portion 42 (52) located in wetness sensing area 420 (520) would vary with urine volume increases, and the sensing purpose is thus achieved.

Figure 6A:
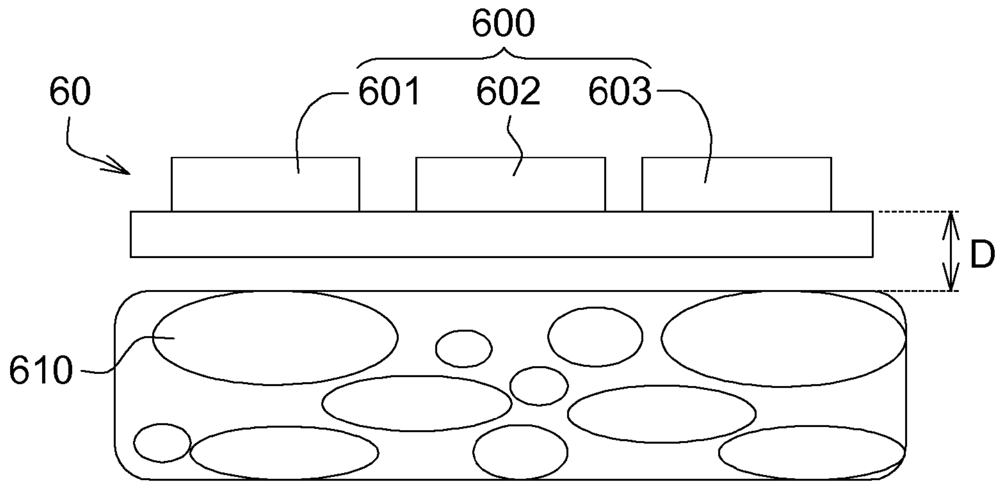
FIGS. 6A-6B respectively are schematic diagrams of RF identification tags and absorbers according to another application example of the disclosure.

Referring to FIG. 6A, the RF identification tag 60 is disposed on one side of the absorber 610. The RF electromagnetic waves of the RF identification tag are spread between the signal conductors 602 of the coplanar waveguide structure 600 and its neighboring ground conductors, namely, the ground conductors 601 and 603. Therefore, when the dielectric material between the signal conductors 602 and its neighboring ground conductors 601 and 603 changes, the distribution of the electromagnetic waves will change and cause the characteristic impedance of the coplanar waveguide structure 600 to change accordingly. The coplanar waveguide structure 600 may sense the change in dielectric material within a distance of 1 mm. When the gap D is larger than 1 mm, the impedance of the coplanar waveguide structure 600 is no longer affected by the absorber 610.

Figure 6B:
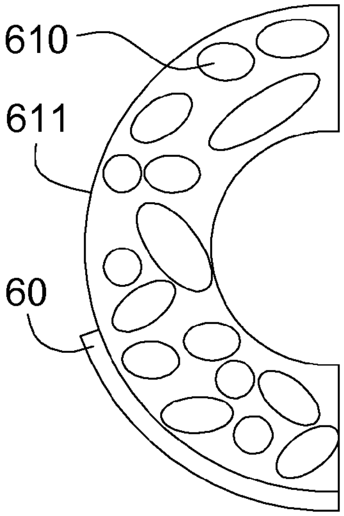

FIG. 6B shows an application example in which the RF identification tag 60 and the absorber 610 do not have direct contact. The RF identification tag 60 and the absorber 610 are separated from each other by an impermeable outer layer 611. The thickness of the impermeable outer layer 611 is such as smaller than or equal to 1 mm (that is, the gap D is smaller than or equal to 1 mm). In other words, when the gap between the RF identification tag 60 and the absorber 610 is smaller than or equal to 1 mm, the RF identification tag 60 will be able to sense the wetness state of the absorber 610 without directly contacting the absorber 610.

In general, the wet location is in the crotch, and the antenna portion of an ordinary RF identification tag is disposed in the crotch and cannot extend its length to the outside of the crotch. Therefore, the signal received by the antenna portion may easily be shielded by human body, and result in erroneous actions. Conversely, the RF identification tag 40 (50) of the present embodiments extends the planar antenna 43 (53) to the outside of the urine wetness sensing area 420 (520) through the adjustment in the length of the transmission portion (refer to FIGS. 3A-3C). In an embodiment, the planar antenna 43 (53) may be located in the buttock area behind the crotch. The buttock area is one area 430 (530) in which the RF signal is stably read. In the present embodiment, the length of the transmission portion is adjustable, and ranges between 3-15 cm to achieve the separation design with the impedance match portion being located in urine wetness sensing area and the planar antenna being located in the reading area.

Figure 7:
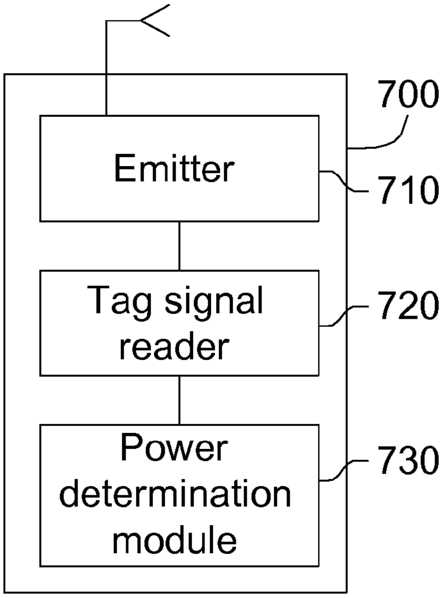
FIG. 7 shows a schematic diagram of a host of a wetness sensing system according to an application example of the disclosure.

Referring to FIG. 7, a schematic diagram of a host 700 of a wetness sensing system according to an application example of the disclosure is shown. The host of wetness sensing system may sense wetness in cooperation with any one of the urine wetness sensing diapers 4*a*-4*b* and wetness sensing absorbers 5*a*-5*b* illustrated in FIGS. 4A-4B and FIGS. 5A-5B. The host 700 of the sensing system includes an emitter 710, and a tag signal reader 720. The emitter 710 emits an RF signal for exciting the RF chip to generate an identification code. The tag signal reader 720 reads the identification code emitted from the RF chip. However, when the RF energy is lower than a predetermined value, this indicates that the RF chip is not excited and the tag signal reader 720 is unable to read the signal transmitted from the RF chip. Meanwhile, the host 700 of the sensing system may receive the sensing results obtained by the RF identification tag 40 (50), and accordingly send out a notification. For example, when the signal indicates that the sensed urine volume and wetness level meet the conditions of a warning state, the host 700 may emit a warning signal to inform the parents or caregivers to replace the diaper or absorber. In an embodiment, the host 700 of the sensing system may further include a power determination module 730, which reads an RF energy level emitted from the RF chip, and further determines whether the received energy reaches the warning level. For example, if the signal indicates that sensed urine volume and wetness or other environmental factors have not yet reached the warning level, the host 600 of the sensing system does not emit any warning signals.

An RF identification tag and a diaper, an absorber and sensing system using the same are disclosed in above embodiments of the disclosure. The RF identification tag with wetness sensing function may be designed according to the length. The antenna portion and the sensor unit (that is, the impedance match portion of the coplanar waveguide transmission line structure) of the RF identification tag are separated by a predetermined distance to achieve stable signal reading and meet the requirements of wetness sensing. In addition, the design of including a coplanar waveguide structure in the RF identification tag not only is easy to manufacture and implement, but also increases sensing sensitivity and achieves broadband effect.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A radio frequency (RF) identification tag with coplanar waveguide structure, comprising:

a substrate;

a planar antenna and an RF chip disposed on the substrate; and a coplanar waveguide structure, disposed on the substrate and coupled to the planar antenna, wherein the coplanar waveguide structure is composed of a plurality of signal conductors and a plurality of ground conductors interlaced on two opposite sides of the signal conductors, and the coplanar waveguide structure comprises:

an impedance match portion having an input end and a ground plane, wherein the input end is coupled to the signal conductors, the ground plane is coupled to the ground conductors, and the RF chip is disposed between the input end and the ground plane, wherein the signal conductors comprise a first signal conductor, a second signal conductor and a third signal conductor, and the ground conductors comprise a first ground conductor, a second ground conductor, a third ground conductor and a fourth ground conductor, wherein the first signal conductor is located between the first ground conductor and the second ground conductor, and the first signal conductor is coupled to the input end and the ground plane or the first ground conductor, such that the first signal conductor, the first ground conductor and the second ground conductor together constitute a first shorted transmission line;

the second signal conductor is located between the second ground conductor and the third ground conductor, the second signal conductor is coupled to the input end and the ground plane, and the RF chip is coupled to the second signal conductor, such that the second signal conductor, the second ground conductor and the third ground conductor together constitute an RF signal transmission line; and the third signal conductor is located between the third ground conductor and the fourth ground conductor, and the third signal conductor is coupled to the input end and the ground plane or the fourth ground conductor, such that the third signal conductor, the third ground conductor and the fourth ground conductor together constitute a second shorted transmission line; and a transmission portion connected between the impedance match portion and the planar antenna.

2. The Radio Frequency identification tag according to claim 1, wherein the first signal conductor and the third signal conductor extend in an S shape.

3. The Radio Frequency identification tag according to claim 1, wherein the planar antenna is a dipole antenna comprising a first radiator and a second radiator, the first radiator connects the second signal conductor, and the second radiator connects the fourth ground conductor.

4. The RF identification tag according to claim 3, further comprising a jumper connecting the first ground conductor and the fourth ground conductor.

5. The Radio Frequency identification tag according to claim 3, further comprising a ground conductors connected between the first radiator and the first ground conductor.

6. The Radio Frequency identification tag according to claim 1, wherein the planar antenna is a monopole antenna comprising a radiator, which connects the second signal conductor.

7. The Radio Frequency identification tag according to claim 1, wherein widths of the first ground conductor, the second signal conductor and the fourth ground conductor are distributed in the transmission portion in the shape of a strip or ladder.

8. A urine wetness sensing diaper, comprising:

a permeable inner layer;

an impermeable outer layer;

an absorber interposed between the inner layer and the outer layer; and a Radio Frequency identification tag with the coplanar waveguide structure according to claim 1 disposed on one side of the absorber.

9. The urine wetness sensing diaper according to claim 8, wherein a gap between the Radio Frequency identification tag and the absorber is smaller than or equal to 1 mm.

10. The urine wetness sensing diaper according to claim 8, wherein the impermeable outer layer is located between the Radio Frequency identification tag and the absorber, and a thickness of the impermeable outer layer is smaller than or equal to 1 mm.

11. A urine wetness sensing system, comprising:

an emitter for generating an Radio Frequency (RF) signal;

a urine wetness sensing diaper according to claim 8, wherein the RF chip receives the RF signal and generates an identification code; and a tag signal reader for reading the identification code emitted from the RF chip.

12. The urine wetness sensing system according to claim 11, further comprising:

a power determination module for determines whether the RF energy emitted from the RF chip reaches warning level.

13. A wetness sensing absorber, comprising:

a permeable inner layer;

an impermeable outer layer;

an absorber interposed between the inner layer and the outer layer; and an Radio Frequency identification tag with the coplanar waveguide structure according to claim 1 disposed on one side of the absorber.

14. The wetness sensing absorber according to claim 13, wherein a gap between the Radio Frequency identification tag and the absorber is smaller than or equal to 1 mm.

15. The wetness sensing absorber according to claim 13, wherein the permeable outer layer is located between the Radio Frequency identification tag and the absorber, and a thickness of the impermeable outer layer is smaller than or equal to 1 mm.

16. A wetness sensing system, comprising:

an emitter for generating an Radio Frequency (RF) signal;

a wetness sensing absorber according to claim 13, wherein the RF chip receives the RF signal and generates an identification code; and a tag signal reader for reading the identification code emitted from the RF chip.

17. The wetness sensing system according to claim 16, further comprising:

a power determination module for determining whether the RF energy emitted from the RF chip reaches warning level.

* * * * *